United States Patent
Chen et al.

(10) Patent No.: US 7,452,366 B2
(45) Date of Patent: Nov. 18, 2008

(54) SAFETY LANCET DEVICE

(75) Inventors: Tzer-Ming Chen, Taipei (TW); Fu-Yuan Li, Taipei (TW)

(73) Assignee: Eumed Biotechnology Co., Ltd., Sanchung, Taipei Hsien (TW)

( * ) Notice: Subject to any disclaimer, the term of this patent is extended or adjusted under 35 U.S.C. 154(b) by 961 days.

(21) Appl. No.: 10/840,709

(22) Filed: May 6, 2004

(65) Prior Publication Data

US 2005/0251188 A1    Nov. 10, 2005

(51) Int. Cl.
*A61B 17/32* (2006.01)
(52) U.S. Cl. .................................. 606/181; 606/182
(58) Field of Classification Search ............... 606/181, 606/182, 184; 600/583
See application file for complete search history.

(56) References Cited

U.S. PATENT DOCUMENTS

| | | | | |
|---|---|---|---|---|
| 4,388,925 A * | 6/1983 | Burns | ............ | 606/182 |
| 4,653,513 A * | 3/1987 | Dombrowski | ............ | 600/578 |
| 5,147,375 A * | 9/1992 | Sullivan et al. | ............ | 606/182 |
| 5,318,584 A * | 6/1994 | Lange et al. | ............ | 606/182 |
| 5,350,392 A * | 9/1994 | Purcell et al. | ............ | 606/182 |
| 5,540,709 A * | 7/1996 | Ramel | ............ | 606/183 |
| RE35,803 E * | 5/1998 | Lange et al. | ............ | 606/182 |
| 5,879,311 A * | 3/1999 | Duchon et al. | ............ | 600/583 |
| 5,908,434 A * | 6/1999 | Schraga | ............ | 606/181 |
| 5,984,940 A * | 11/1999 | Davis et al. | ............ | 606/181 |
| 6,419,661 B1 * | 7/2002 | Kuhr et al. | ............ | 604/207 |
| 6,540,762 B1 | 4/2003 | Bertling | | |
| 6,949,111 B2 * | 9/2005 | Schraga | ............ | 606/182 |
| 2003/0199892 A1 * | 10/2003 | Kim | ............ | 606/181 |
| 2004/0186500 A1 * | 9/2004 | Koike et al. | ............ | 606/181 |

FOREIGN PATENT DOCUMENTS

| | | |
|---|---|---|
| DE | 20012784 | 4/2001 |
| EP | 0622046 A2 | 11/1994 |
| JP | 07-016218 A | 1/1995 |
| JP | 08-084721 A | 4/1996 |
| JP | 2000-245717 A | 9/2000 |
| JP | 2004-113580 A | 4/2004 |
| WO | 97/42886 | 11/1997 |

* cited by examiner

*Primary Examiner*—Darwin P Erezo
(74) *Attorney, Agent, or Firm*—patenttm.us (57) ABSTRACT

A safety lancet device has a casing, a driver assembly and a needle hub with a needle. The driver assembly and the needle hub are mounted within the casing. The driver assembly comprises a container, a pressing unit, a controller, a pushing unit and a resilient unit. The needle hub is controlled by the driver assembly to make the needle momentarily protrude. After the needle is used, the location of the driver assembly keeps the needle from protruding. When a new needle hub replaces the used needle hub, the driver assembly will return to the original location before use and can drive the needle momentarily from the casing. Users will not forget to change the used needle. Furthermore, the safety lancet device will decrease the danger of infection.

19 Claims, 12 Drawing Sheets

SAFETY LANCET DEVICE

BACKGROUND OF THE INVENTION

1. Field of the Invention

The present invention relates to a safety lancet device, and more particularly to a safety lancet device for obtaining small blood samples, which mounts a new needle hub within the safety lancet device to obtain each blood sample.

2. Description of Related Art

To take small amounts of blood from the finger or the earlobe for diagnostic purposes, lancets are used to prick the corresponding body part either manually or with the aid of a simple apparatus. The lancet has to be sharp and sterile. However, if the force applied to the lancet is not large enough, the lancet will not prick the body part.

Furthermore, a conventional lancet device used for taking small amounts of blood is like a mechanical pencil. The conventional lancet device comprises a top thumb tab, a casing, a driver assembly and a needle hub with a needle. The top thumb tab, the driver assembly and the needle hub are mounted within the casing. The top thumb tab is attached on the driver assembly and the driver assembly is attached on the needle hub. After pressing the top thumb tab, the driver assembly forces the needle to protrude from the needle hub. However, the used needle hub of the conventional lancet device can continue to be use so users may forget to replace the used needle hub with a new needle hub. In which case, the used needle in the needle hub will prick the next patient. If the used needle is contaminated, the person may be infected.

SUMMARY OF THE INVENTION

The main objective of the present invention is to provide a safety lancet device that will necessitate that a new needle hub be installed before each use.

To achieve the objective, a safety lancet device in accordance with the present invention comprises a casing, a driver assembly and a needle hub with a needle. The driver assembly and the needle hub are mounted inside the casing. The driver assembly comprises a container, a pressing unit, a controller, a pushing unit and a resilient element. The pressing unit is mounted around the pressing unit. The controller is mounted in the container, and the pushing unit is mounted in the controller. The resilient element is mounted between the pushing unit and the casing. The needle hub is inserted into the container and controlled by the driver assembly push the needle out. After the needle is used, the location of the pressing unit, the controller and the pushing unit keeps the needle from protruding from the casing. When a new needle hub replaces the used needle hub, the pressing unit, the controller and the pushing unit will return to their original locations. People will not forget to change the used needle because the device cannot be operated with a used needle. Furthermore, the safety lancet device will decrease the danger of infection.

Further benefits and advantages of the present invention will become apparent after a careful reading of the detailed description with appropriate reference to the accompanying drawings.

DETAILED DESCRIPTION OF THE INVENTION

Figure 1:
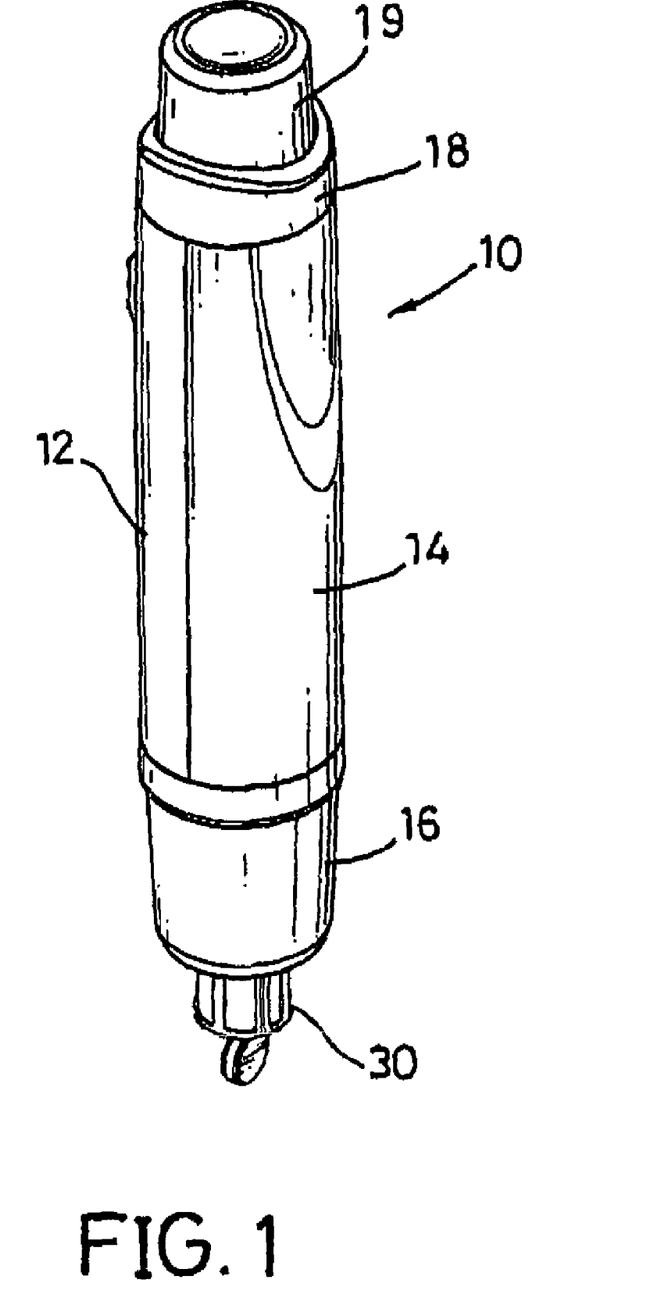
FIG. 1 is a perspective view of a safety lancet device in accordance with the present invention.
Figure 2:
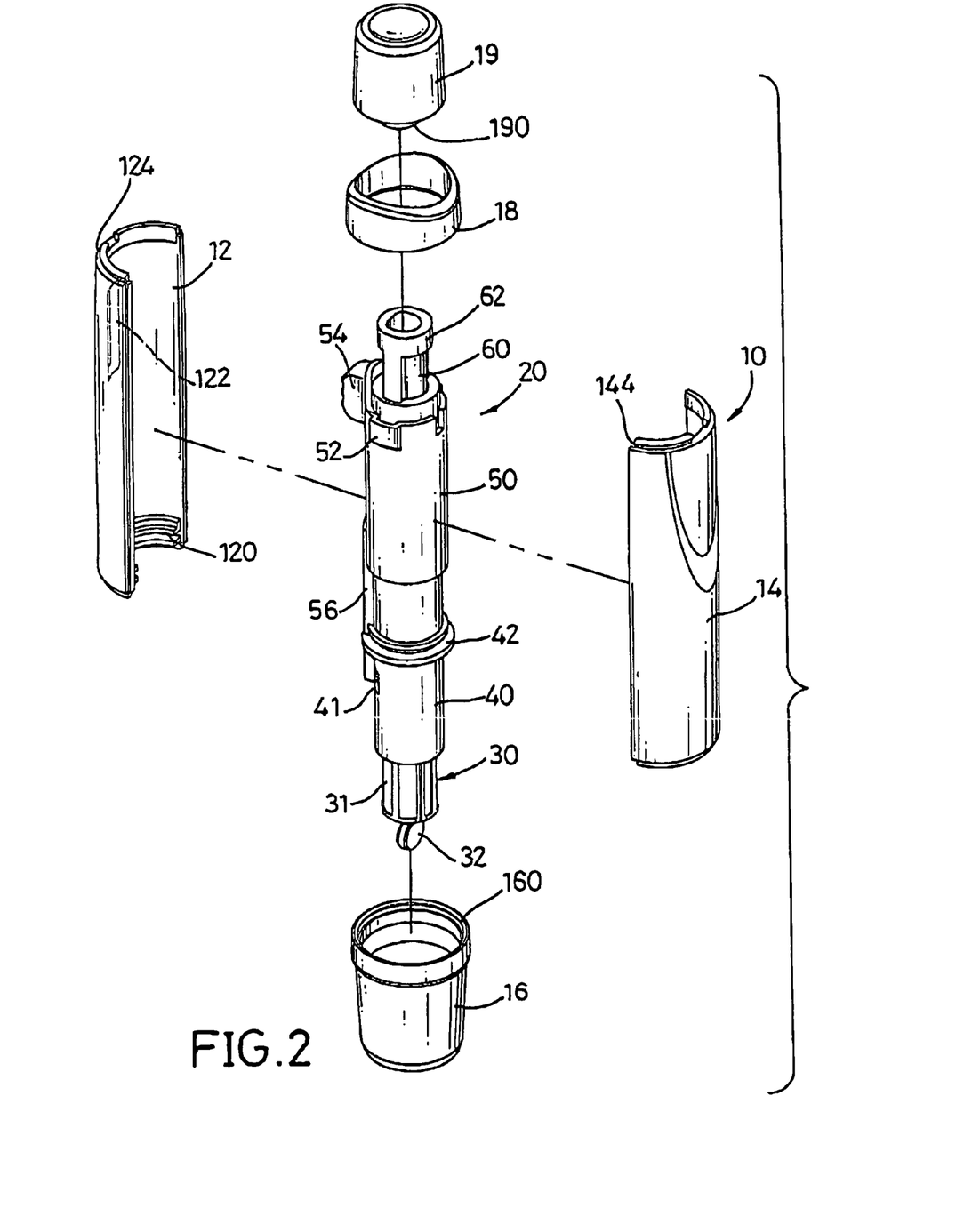
FIG. 2 is a partially exploded perspective view of the safety lancet device in FIG. 1.

With reference to FIGS. 1 and 2, a safety lancet device in accordance with the present invention comprises a casing (10), a driver assembly (20) and a needle hub (30).

The casing (10) preferably comprises a front casing (12), a rear casing (14), a bottom ring (16), a top ring (18) and a top cap (19).

The front casing (12) comprises a proximal end (not numbered), a distal end (not numbered), an inner surface (not numbered), an outer surface (not numbered), multiple annular ribs (120), a guide slot (122) and multiple recesses (124). The multiple annular ribs (120) are formed around and extend radially inward from the inner surface near the proximal end. Preferably, the front casing (12) has two annular ribs (120). The guide slot (122) is formed longitudinally through the front casing (12) near the distal end. The recesses (124) are formed radially around and inward from the outer surface respectively of the distal end and the proximal end. Preferably, the proximal end and the distal end have respectively a recess (124).

Figure 5A:
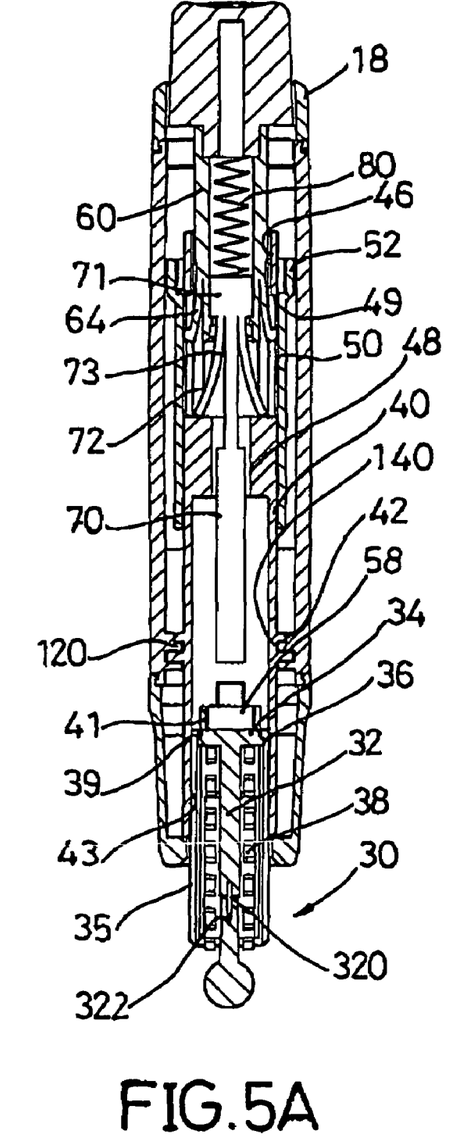
FIG. 5A is a cross sectional front view of the safety lancet device in FIG. 1 before being used.
Figure 5B:
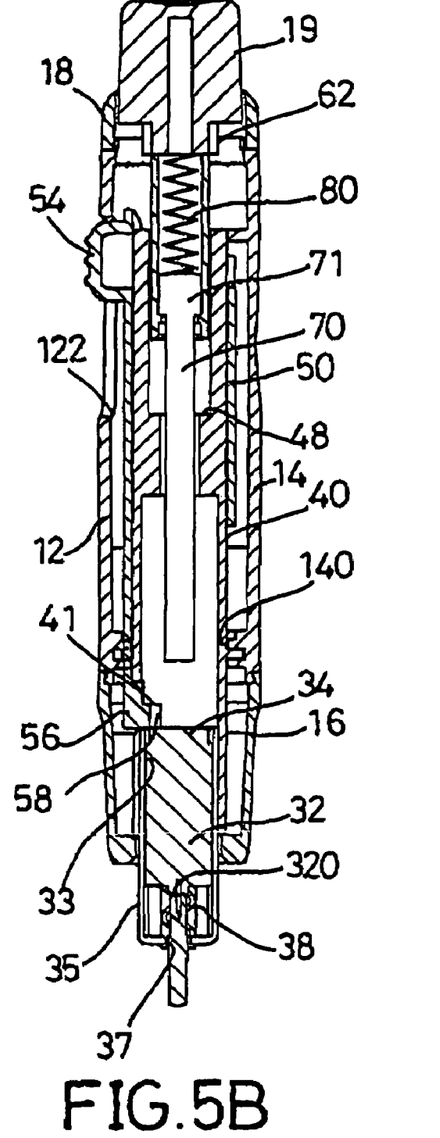
FIG. 5B is a cross sectional side view of the safety lancet device in FIG. 5A.

With further reference to FIGS. 5A and 5B, the rear casing (14) engages the front casing (12) to form a cylindrical casing and comprises a proximal end (not numbered), a distal end (not numbered), an inner surface (not numbered), an outer surface (not numbered), multiple annular ribs (140) and multiple recesses (144). The multiple annular ribs (140) are formed around and extend radially inward from the inner surface near the proximal end and correspond to the annular ribs (120) on the front casing (12). Preferably, the rear casing (20) has two annular ribs (140). The recesses (144) are formed around and extend radially inward from the outer surface respectively at the distal end and the proximal end and correspond to the recesses (124) on the front casing (12). Preferably, the proximal end and the distal end have a recess (144).

The bottom ring (16) optionally is cylindrical, comprises a proximal end (not numbered), a distal end (not numbered), an inside surface (not numbered) and an annular ring (160) and engages the proximal ends of the front casing (12) and the rear casing (14). The annular ring (160) is formed on the inside surface, extends radially inward from the proximal end of the bottom ring (16) and engages the recesses (124, 144) in the proximal ends of the front casing (12) and the rear casing (14).

The top ring (18) engages the distal ends of the front casing (12) and the rear casing (14). The top cap (19) comprises a proximal end (190) and a distal end (not numbered). The proximal end (190) passes through the top ring (16) and is attached to the driver assembly (20). Preferably, the proximal end (190) has an outer surface (not numbered) and an outer thread (not shown) formed on the outer surface.

Figure 3:
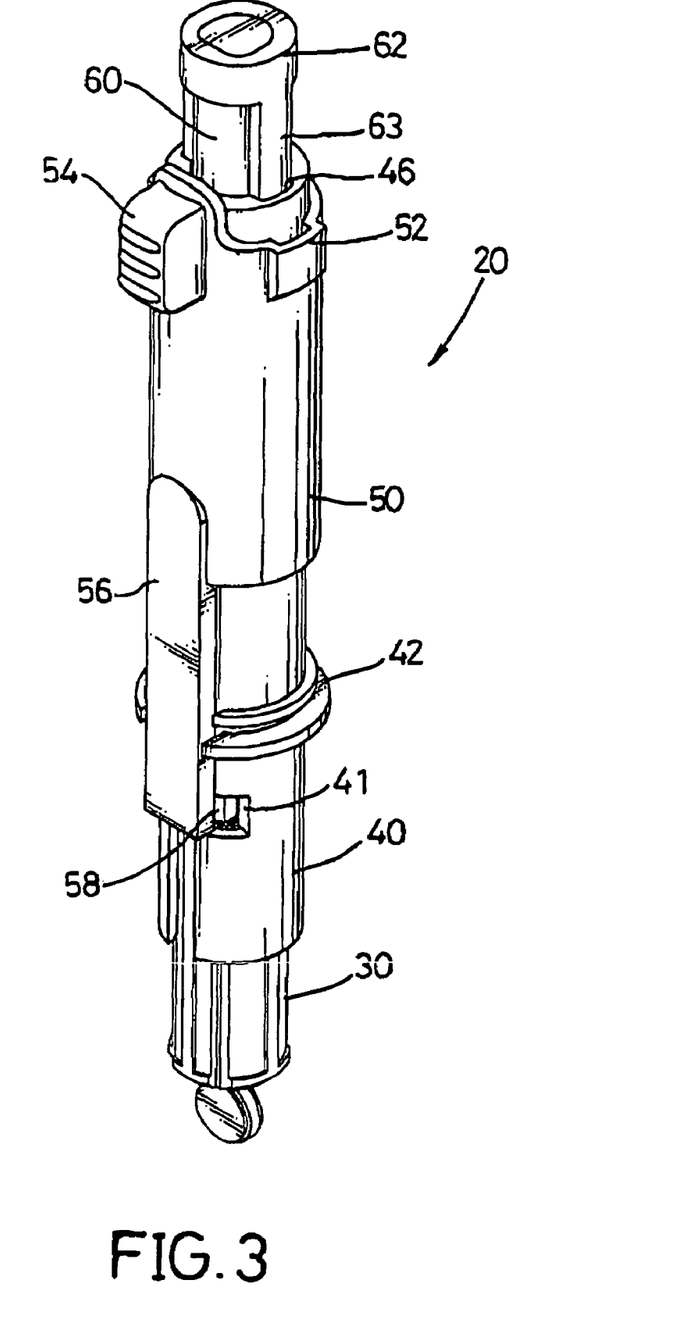
FIG. 3 is a perspective view of a driver assembly of the safety lancet device in FIG. 1.
Figure 4:
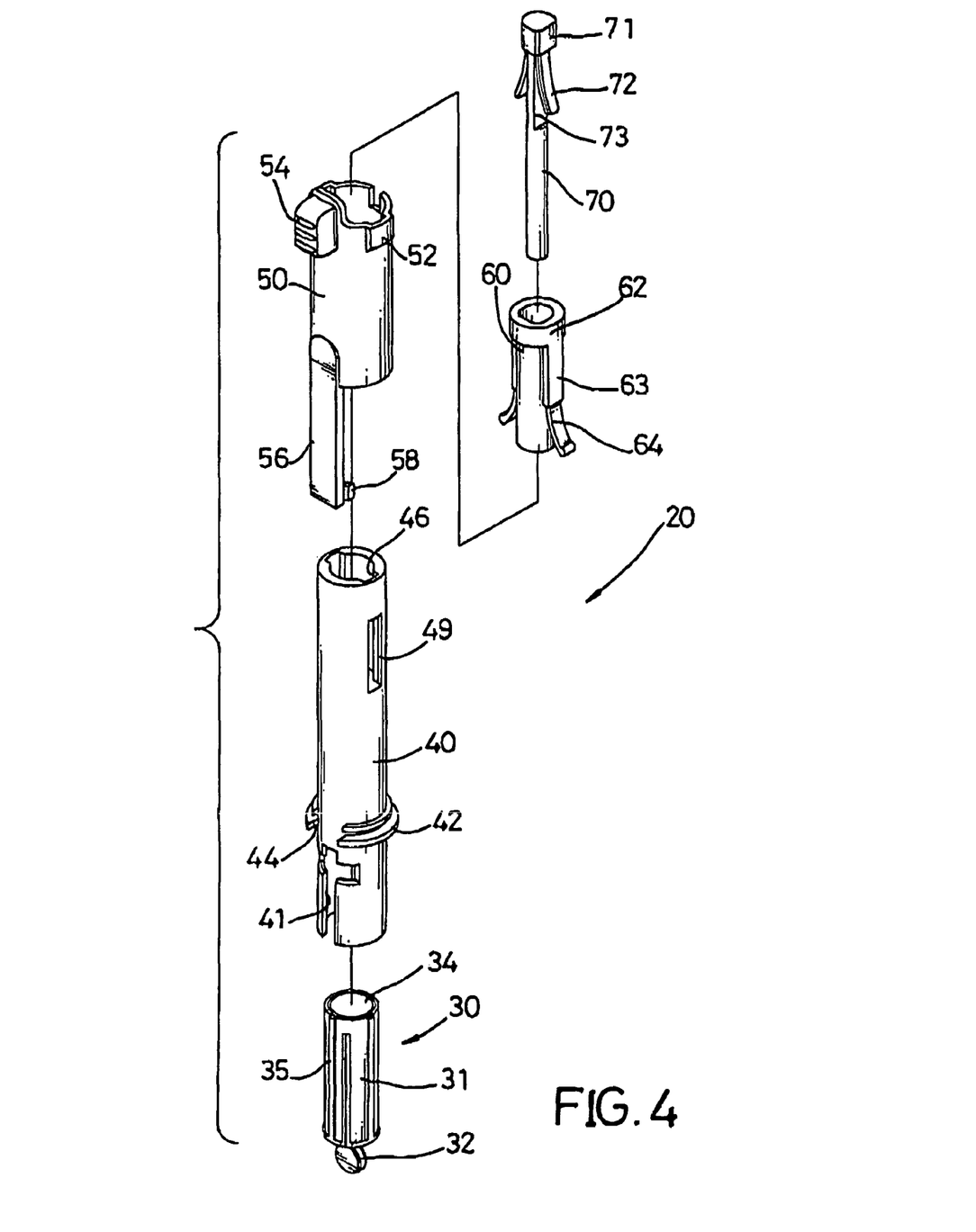
FIG. 4 is an exploded perspective view of the driver assembly in FIG. 3.

With further reference to FIGS. 3 to 5, the driver assembly (20) is mounted in the casing (10) and comprises a container (40), a pressing unit (50), a controller (60), a pushing unit (70) and a resilient element (80).

The container (40) is cylindrical, is mounted securely in the casing (10) and comprises a proximal open end (not numbered), a distal open end (not numbered), an inner surface (not numbered), an outer surface (not numbered), an outer diameter (not numbered), an inner diameter (not numbered), a middle (not numbered), an optional slot (41), multiple optional annular flanges (42), multiple optional longitudinal recesses (43), multiple optional gaps (44), multiple optional grooves (46), an annular protrusion (48) and multiple side slots (49). The optional slot (41) is formed through the proximal open end and has a cross shape. The multiple annular flanges (42) are formed around and extend radially outward from the outer surface near the middle. Preferably, the container (40) has two annular flanges (42). The multiple optional longitudinal recesses (43) are formed longitudinally in the inner surface at the proximal open end. The optional gaps (44) are formed respectively in the annular flange (42). The multiple optional grooves (46) are formed longitudinally in the inner surface of the distal open end. Preferably, the container (40) has two grooves (46). The annular protrusion (48) is formed integrally with and extends inward from the inner surface in the middle and has an inner surface (not numbered), an inner diameter (not numbered) and a top (not numbered). The side slots (49) are formed through the outer surface, between the annular protrusion (48) and the distal open end and comprise a top (not numbered) and a bottom (not numbered). Preferably, the container (40) has two side slots (49).

The pressing unit (50) is cylindrical, is mounted slidably around the distal open end of the container (40) and comprises a proximal end (not numbered), a distal end (not numbered), an inner diameter (not numbered), multiple protruding keys (52), an optional thumb tab (54), a rod (56) and an optional tab (58). The inner diameter of the pressing unit (50) corresponds to the outer diameter of the container (40). Each protruding key (52) has a bottom (not numbered) and is formed integrally with and extends outward from the distal end. Preferably, the pressing unit (50) has two protruding keys (52). The optional thumb tab (54) is formed on and extends outward from the distal end. The rod (56) is formed on and extends downward from the proximal end and has a free end (not numbered). The optional tab (58) is formed on and extends inward from the free end of the rod (56).

Figure 6A:
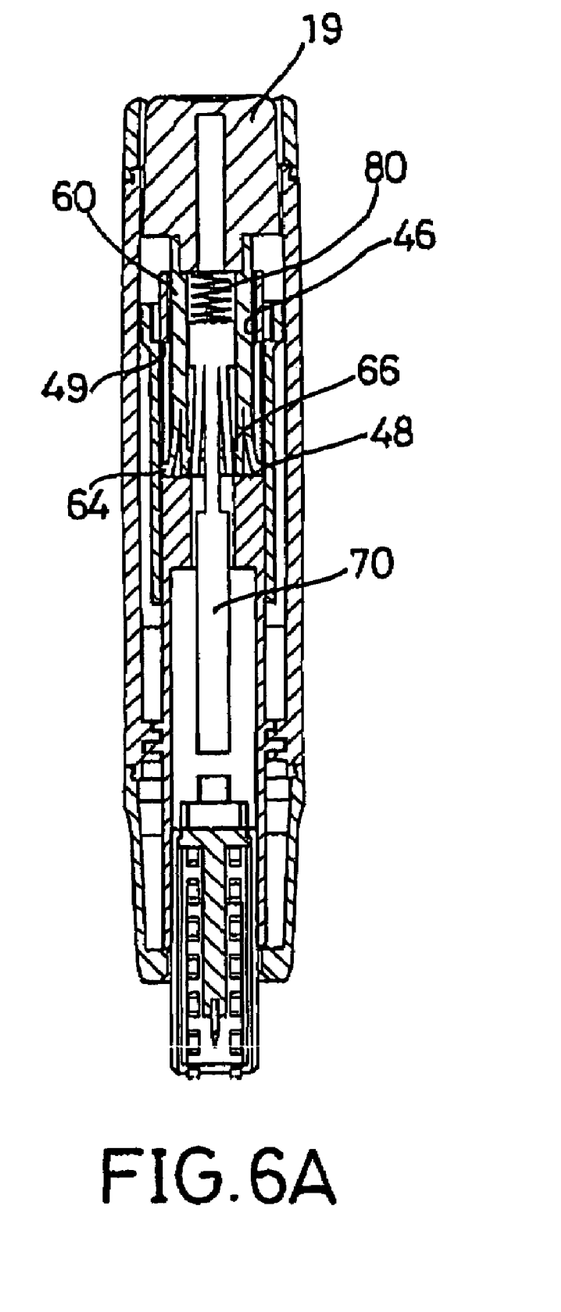
FIG. 6A is an operational cross sectional front view of the safety lancet device in FIG. 1 with a top cap of the safety lancet device pressed.

With further reference to FIG. 6A, the controller (60) is cylindrical, is mounted slidably in the distal open end of the container (40) and comprises a proximal end (not numbered), a distal end (not numbered), an outer diameter (not numbered), an outer surface (not numbered), an inner surface (not numbered), an optional top annular ring (62), multiple optional longitudinal ribs (63), multiple arced controller tabs (64), an inner annular ring (66) and an optional inner threaded (not shown). The outer diameter of the controller (60) corresponds to the inner diameter of the container (40). The optional annular ring (62) is formed on and extends radially outward from the outer surface of the proximal end. Each arced controller tab (64) has an attached end (not numbered) and a free end (not numbered). The attached end of the arced controller tab (64) is formed on and extends from the outer surface. The multiple arc controller tabs (64) correspond respectively to the protruding key (52) of the pressing unit (50), the grooves (46) and the side slot (49) of the container (40). Preferably, the controller (60) has two arced controller tabs (64). The multiple optional longitudinal ribs (63) are formed longitudinally on the outer surface and connect to the annular ring (62). Preferably, the arced controller tabs (64) extend respectively from the longitudinal ribs (63). The inner annular ring (66) is formed on and extends radially inward from the inner surface near the distal end and has an inner diameter smaller than the inner diameter of the annular protrusion (48) of the container (40). The optional inner thread is formed on the inner surface of the proximal end.

The pushing unit (70) is slidably mounted in the controller (60) and comprises a proximal closed end (not numbered), a distal closed end (not numbered), an outer diameter (not numbered), a head (71), multiple arced tabs (72) and an optional neck (73). The top cap (19) of the casing (10) is mounted securely on the pushing unit (70). The outer diameter of the pushing unit (70) is smaller than the inner diameter of the inner annular ring (66) in the controller (60). The head (71) is formed on and extends upward from the distal closed end and has an outer diameter. The outer diameter of the head (71) is larger than the inner diameter of the inner annular ring (66) in the controller (60). Each arced tab (72) is formed on and extends downward from the head (71) and has an attached end (not numbered), a free end (not numbered) and an outer diameter (not numbered). The free ends press against the pushing unit (70). The outer diameter of the arced tabs (72) is smaller than the inner diameter of the annular protrusion (48) in the container (40). Preferably, the pushing unit (70) has two arced tabs (72). The optional neck (73) is formed near the distal closed end, and the arced tabs (72) correspond to the neck (73).

The resilient element (80) is mounted between the pushing unit (70) and the top cap (19) of the casing (10).

The needle hub (30) is slidably mounted in the proximal open end of the container (40).

A first embodiment of the needle hub (30) in accordance with the present invention comprises a needle sleeve (31) and a needle core (32).

The needle sleeve (31) comprises a proximal open end (not numbered), a distal closed end (not numbered), an inner surface (not numbered), an outer surface (not numbered), multiple optional longitudinal grooves (33), multiple optional longitudinal ribs (35), a hole (37) and multiple positive limits (39). The multiple optional longitudinal grooves (33) are formed in the inner surface. The multiple optional longitudinal ribs (35) are formed on the outer surface and correspond to the optional longitudinal recesses (43) in the container (40). The hole (37) is formed in the distal closed end. The multiple positive limits (39) are formed respectively on the longitudinal notches (33) near the proximal open end.

The needle core (32) is mounted slidably in the needle sleeve (31), protrudes from the hole (37) and optionally comprises a proximal end (not numbered), a distal end (not numbered), a middle (not numbered), a top plate (34), multiple protrusions (36), multiple resilient core members (38), a detachment joint (320) and a needle (322). The top plate (34) is formed on the proximal end and has an outer surface (not numbered). The multiple protrusions (36) are formed on the outer surface of the top plate (34) and correspond to the longitudinal recesses (33) to limit the needle core (32) in the needle sleeve (31). The resilient core members (38) are attached to the top plate (34) and the distal closed end of the needle sleeve (31) and are mounted between the needle core (32) and the needle sleeve (31). The detachment joint (320) is formed in the middle of the needle core (32), and the needle (322) is attached to the needle core (32) and extends through the detachment joint (320).

Figure 10:
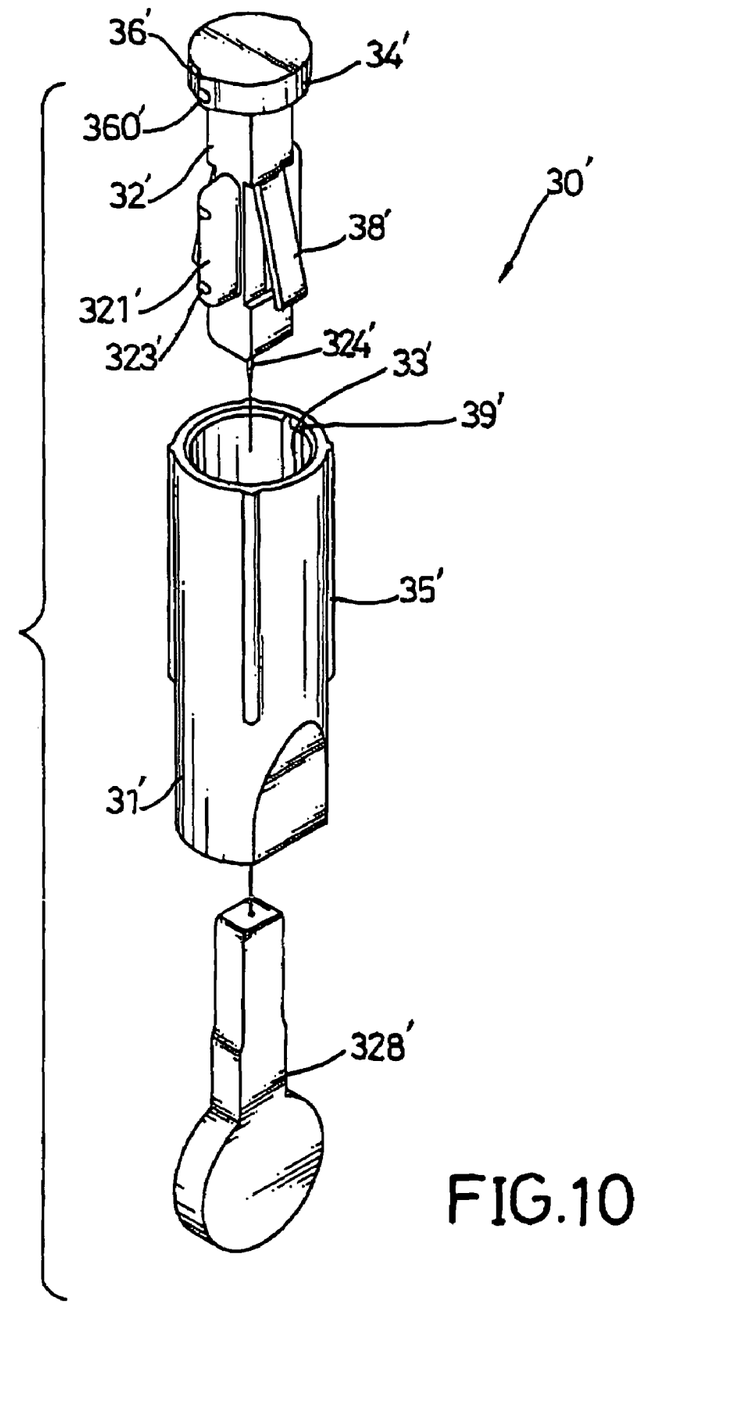
FIG. 10 is an exploded perspective view of another embodiment of a needle hub in accordance with the present invention.
Figure 11:
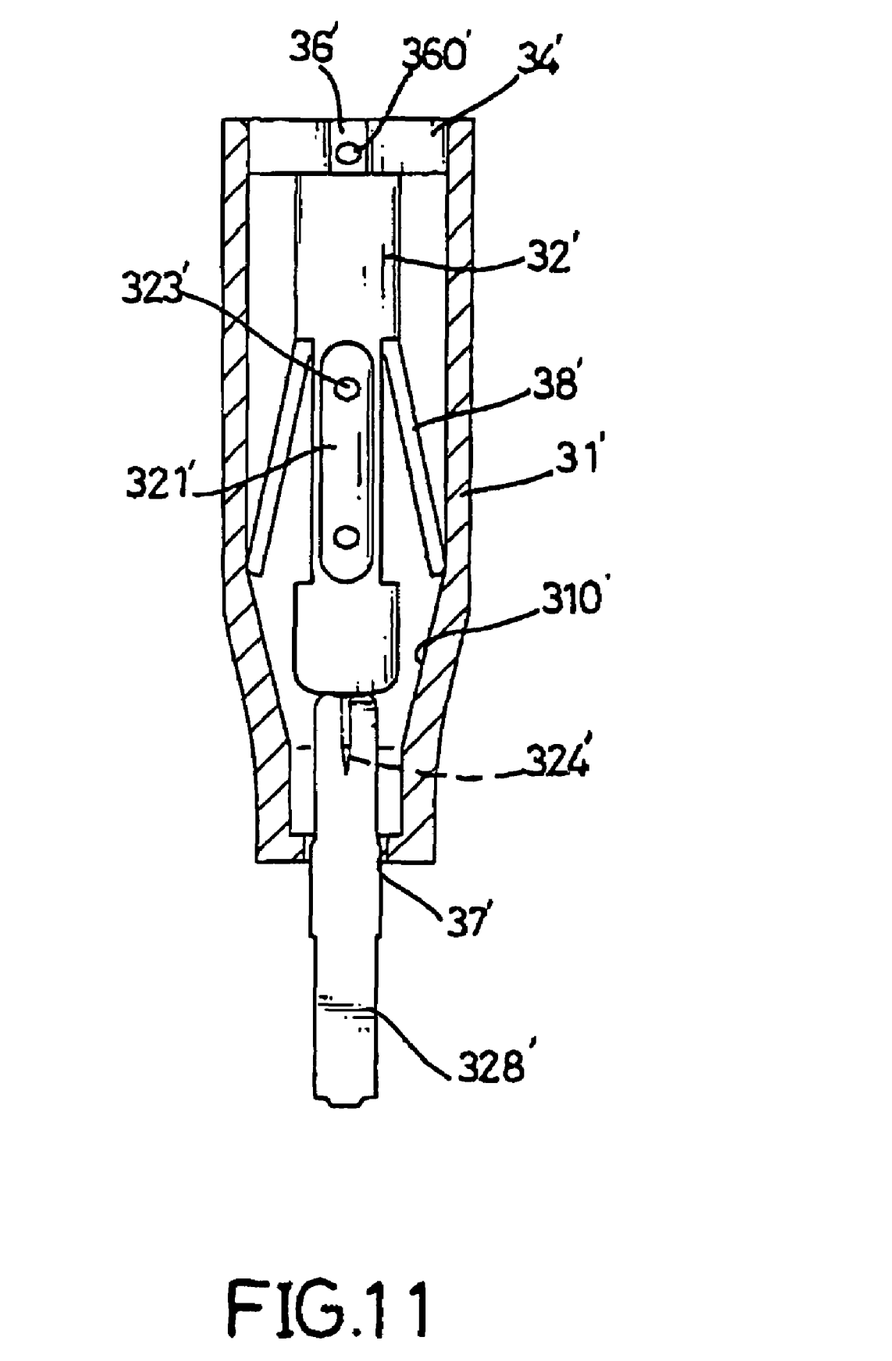
FIG. 11 is a side view in partial section of the needle hub in FIG. 10.
Figure 12:
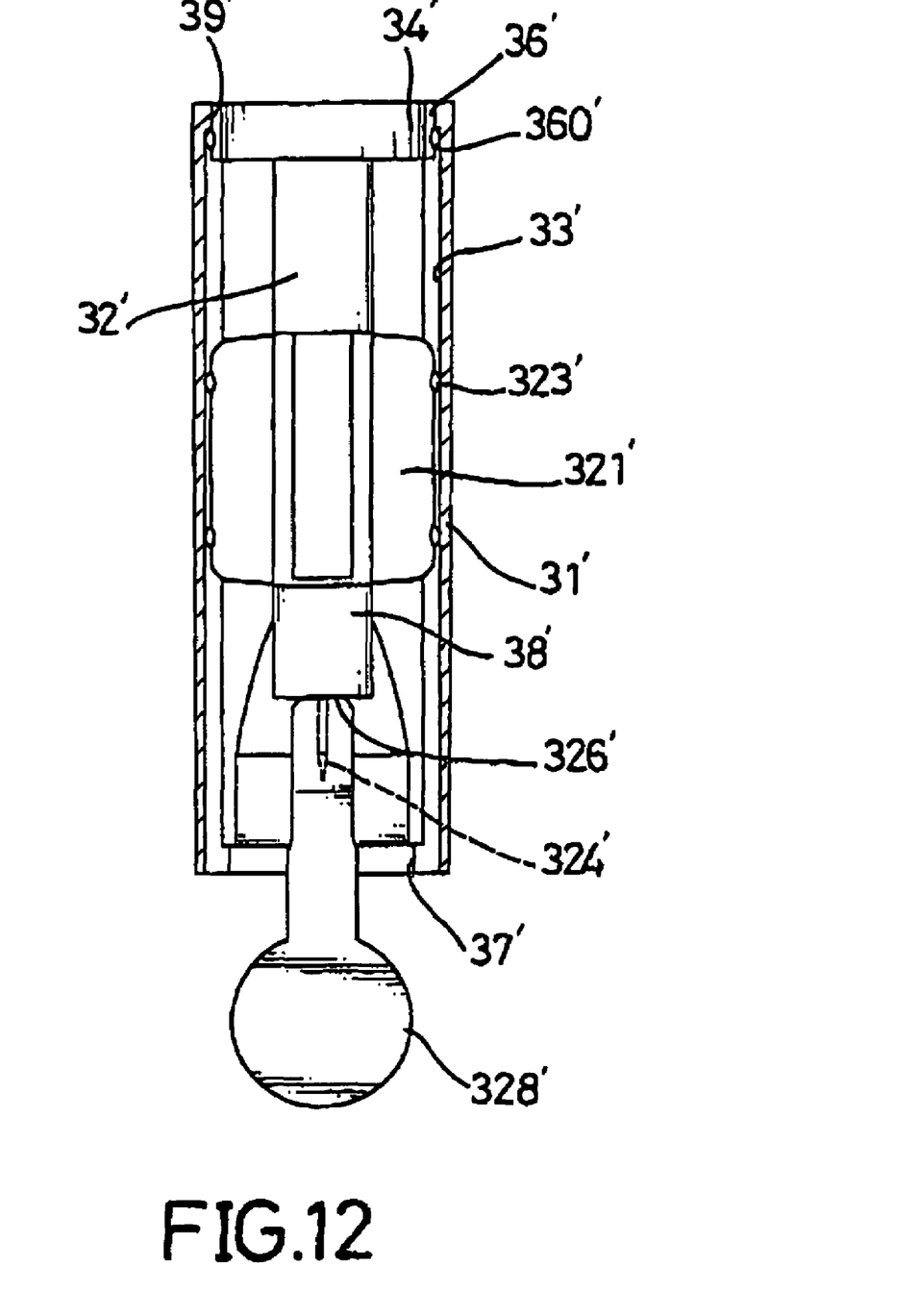
FIG. 12 is a front view in partial section of the needle hub in FIG. 10.

With further reference to FIGS. 10 to 12, a second embodiment of the needle hub (30') comprises a needle sleeve (31') and a needle core (32').

The needle sleeve (31') comprises a proximal open end (not numbered), a distal closed end (not numbered), an inner surface (not numbered), an outer surface (not numbered), multiple optional flat tapers (310'), multiple optional longitudinal grooves (33'), multiple optional longitudinal ribs (35'), a hole (37') and multiple positive limits (39'). The multiple optional longitudinal grooves (33') are formed in the inner surface. The multiple optional longitudinal ribs (35') are formed on the outer surface and correspond to the longitudinal grooves (43) in the container (40). The hole (37') is formed in the distal closed end. The multiple positive limits (39') are formed respectively in the longitudinal grooves (33') near the proximal open end. The multiple flat tapers (310') are formed in the inner surface of the distal closed end.

The needle core (32') is mounted slidably in the needle sleeve (31'), protrudes from the hole (37') and comprises a proximal end (not numbered), a distal end (not numbered), a middle (not numbered), a top plate (34'), multiple protrusions (36'), multiple middle arced tabs (38'), multiple longitudinal keys (321'), a needle (324'), a detachment joint (326') and a needle point sheath (328'). The top plate (34') is formed on the proximal end and has an outer surface (not numbered). The multiple protrusions (36') are formed on the outer surface of the top plate (34'), correspond to the longitudinal recesses (33') to hold the needle core (32') in the needle sleeve (31') and comprise respectively at least one nub (360'). The nub (360') is formed on and extends outward from the protrusions (36') to abut the longitudinal groove (33') in the needle sleeve (31'). The multiple longitudinal keys (321') are formed on and extend outward from the middle of the needle core (32'), correspond respectively to the longitudinal grooves (33') to guide the movement of the needle core (32') and comprise multiple nubs (323'). The multiple nubs (323') are formed on and extend outward from the longitudinal keys (321') to abut the longitudinal grooves (33') in the needle sleeve (31'). Preferably, the needle core (32') has two longitudinal keys (321'). The multiple middle arced tabs (38') are formed on the middle and between the longitudinal keys (321') of the needle core (32') and comprise respectively attached ends (not numbered) and free ends (not numbered). The free ends of the middle arced tabs (38') abuts the flat tapers (310') in the needle sleeve (31'). The detachment joint (326') is formed in the middle of the needle core (32') and separates to form the needle point sheath (328'). The needle (324') is mounted in the middle of the needle core (32') and is located at the detachment joint (326'). After separating the needle point sheath (328') from the needle core (32'), the needle (324') will protrude from the hole (37') in the needle sleeve (31') when the driver assembly (20) pushes the top plate (34') of the needle core (32'). The middle arced tabs (38') will move along the flat tapers (310'), and the needle (324') will protrude from the hole (37') in the needle sleeve (31'). When the pushing force is removed, the tension in the middle arced tabs (38') will return the needle core (32') to the original location, and the needle (324') will draw back into the needle sleeve (31').

The first embodiment of the needle hub (30) is used as the example in the following description.

With further reference to FIGS. 5A and 5B, the driver assembly (20) and the needle hub (30) are mounted in the casing (10) before the safety lancet device is used. The needle hub (30) is inserted into the proximal open end of the container (40), and the longitudinal rib (35) on the needle sleeve (31) engages the longitudinal recesses (43) in the container (40). The container (40) is mounted securely in the front casing (12) and the rear casing (14), and the annular flanges (42) of the container (40) intervene between the annular ribs (120, 140) of the front casing (12) and the rear casing (14). The thumb tab (54) protrudes from the guide slot (122) in the front casing (12). The pressing unit (50) is slidably mounted around the distal open end of the container (40), the rod (56) is located in the gap (44) in the container (40), and the tab (58) is located in the slot (41) in the container (40). The controller (60) is slidably mounted in the distal open end of the container (40) with the longitudinal ribs (63) are mounted respectively in the grooves (46) and the arced controller tabs (64) slidably mounted in the side slot (49) in the container (40). The pushing unit (70) is slidably mounted in the controller (60) and the container (40). The inner annular ring (66) of the controller (60) stops the head (71) of the pushing unit (70), and the arced tabs (72) protrude from the inner annular ring (66) of the controller (60). The free end of the arced tabs (72) are attached to the top of the annular protrusion (48) in the container (40). The resilient element (80) is mounted on the pushing unit (70).

Figure 6B:
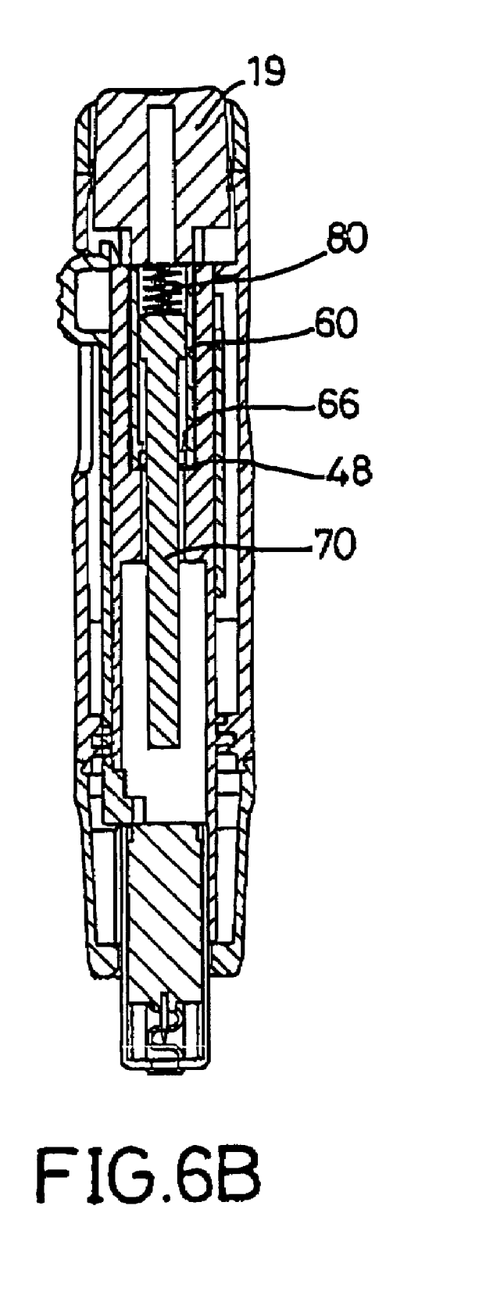
FIG. 6B is an operational cross sectional side view of the safety lancet device in FIG. 6A.

With further reference to FIGS. 6A and 6B, turning and separating the detachment joint (320) of the needle core (32) exposes the needle (322). After pushing the top cap (19), the controller (60) is pushed. The longitudinal ribs (63) move in the grooves (46), and the arced controller tabs (63) move in the side slot (49). Since the arced tabs (72) in the pushing unit (70) still abut the top of the annular protrusion (48), the resilient element (80) is compressed between the top cap (19) and the pushing unit (70).

Figure 7A:
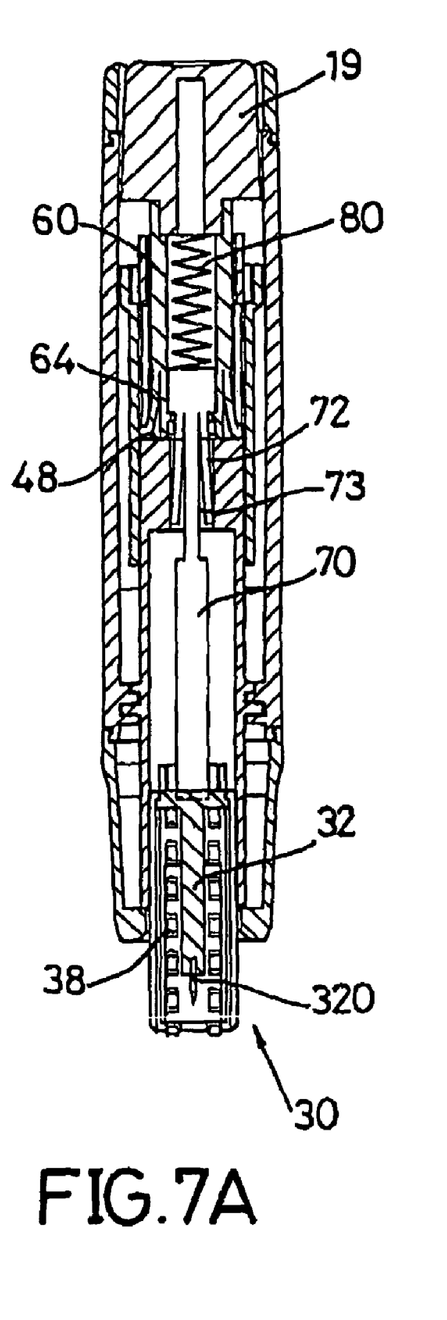
FIG. 7A is an operational cross sectional front view of the safety lancet device in FIG. 1 with a pushing unit pushing a needle hub of the safety lancet.
Figure 7B:
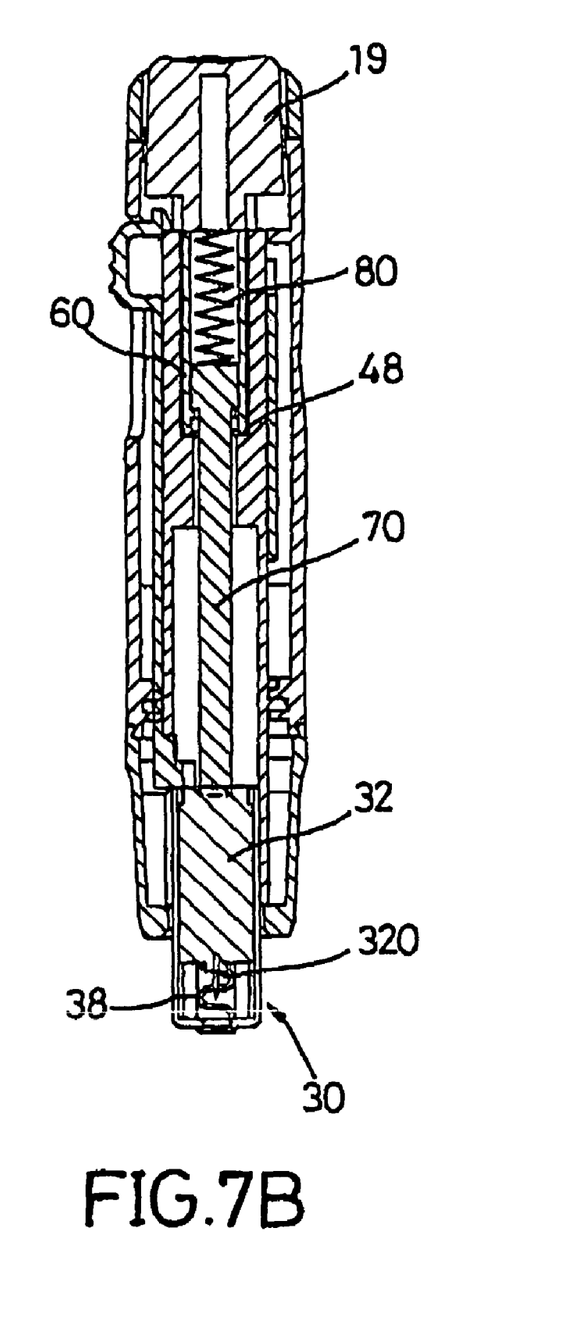
FIG. 7B is an operational cross sectional side view of the safety lancet device in FIG. 7A.

With further reference to FIGS. 7A and 7B, the arced controller tabs (64) move to the bottom of the side slot (49), and the inner annular ring (66) presses the arced tabs (72) against the neck (73) as the resilient element (80) is compressed. When the arced tabs (72) are pressed completely against the neck (73), the arced tabs (72) are released by the annular protrusion (48) and move down inside the inner surface of the annular protrusion (48). The resilient element (80) drives the pushing unit (70) against the needle core (32). The resilient core members (38) are compressed, and the needle (322) protrudes from the hole (37) in the needle sleeve (31) momentarily. The resilient core members (38) press against the top plate (34) and retract the needle (322) back into the needle sleeve (31). The needle (322) will not protrude for any appreciable time so the needle (322) will not prick anyone other than the intended person. With the arced tabs (72) of the pushing unit (70) inside the inner surface of the annular protrusion (48), pushing the top cap (19) again will not have enough force to overcome the resilient core members (38), and the needle (322) will not protrude from the needle sleeve (31).

Figure 8A:
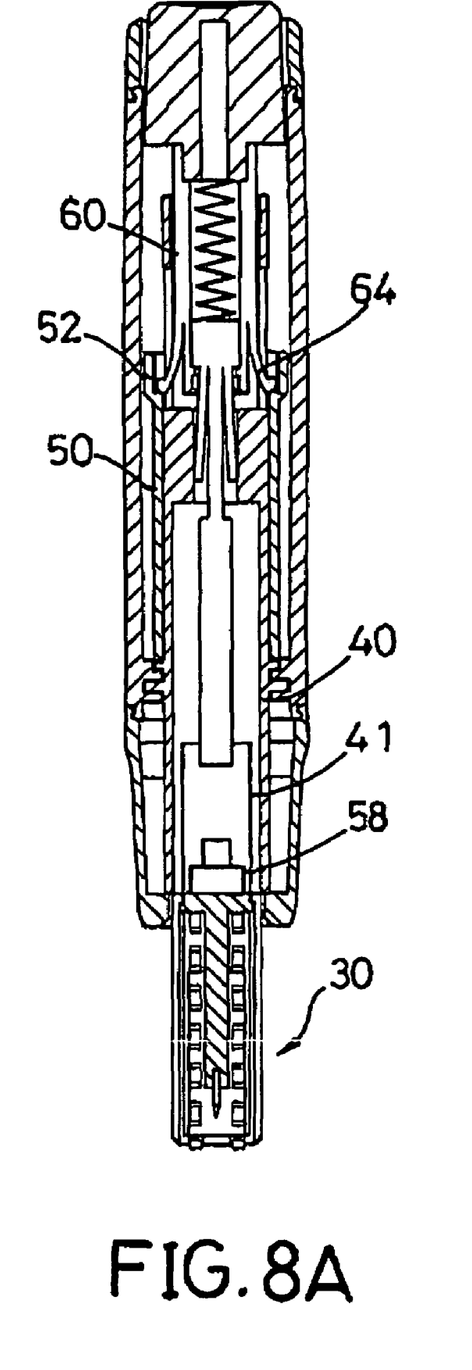
FIG. 8A is an operational cross sectional front view of the safety lancet device in FIG. 1 with a pressing unit to separate the needle hub of the safety lancet pressed.
Figure 8B:
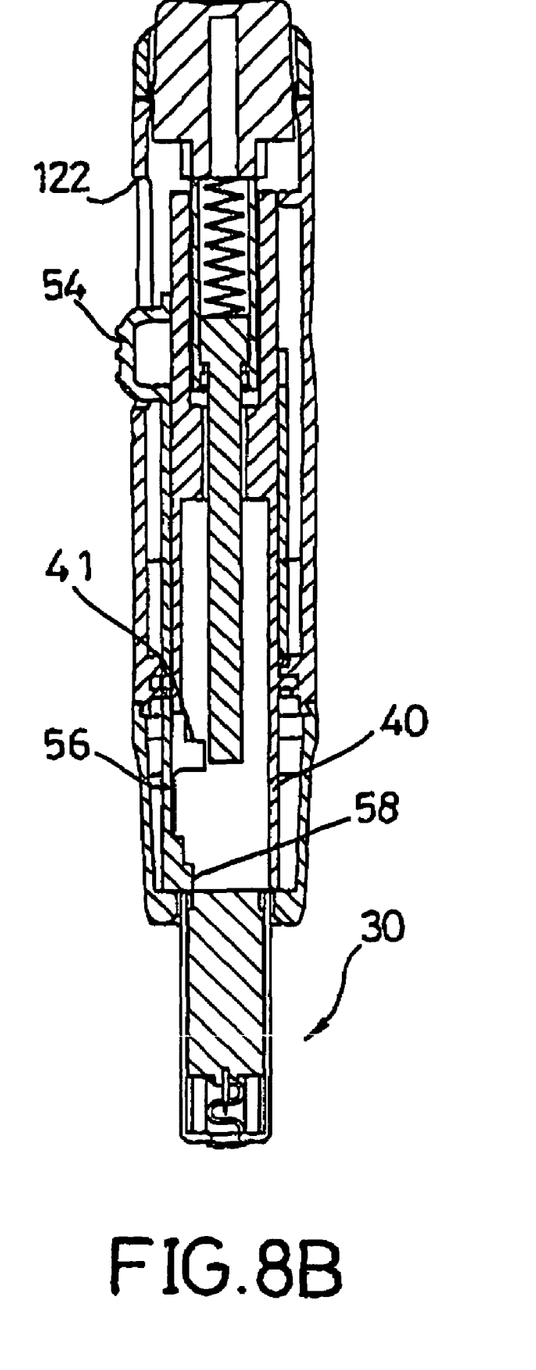
FIG. 8B is an operational cross sectional side view of the safety lancet device in FIG. 8A.

With further reference to FIGS. 8A and 8B, the used needle hub (30) is ejected by pushing the thumb tab (54) on the pressing unit (50) in the guide slot (122) in the front casing (12). The rod (56) with the tab (58) moves in the slot (41) in the container (40), and the tab (58) pushes the needle hub (30) out of the container (40). When the pressing unit (50) is pressed down completely, the protruding keys (52) move below the arced controller tabs (64) that abut the bottom of the protruding keys (52).

Figure 9A:
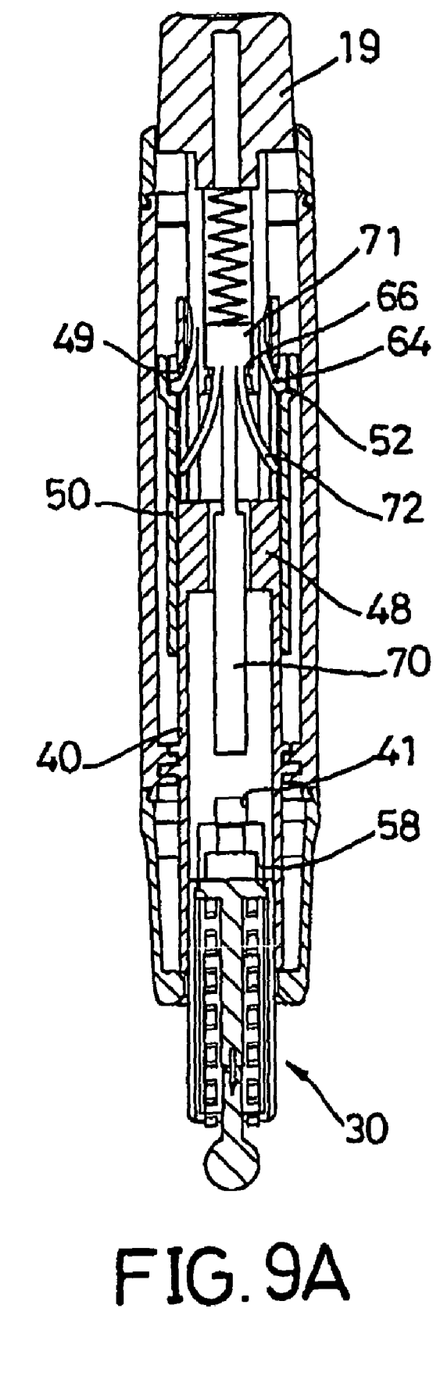
FIG. 9A is an operational cross sectional front view of the safety lancet device in FIG. 1 with a now needle hub being inserted into a container of the safety lancet device.
Figure 9B:
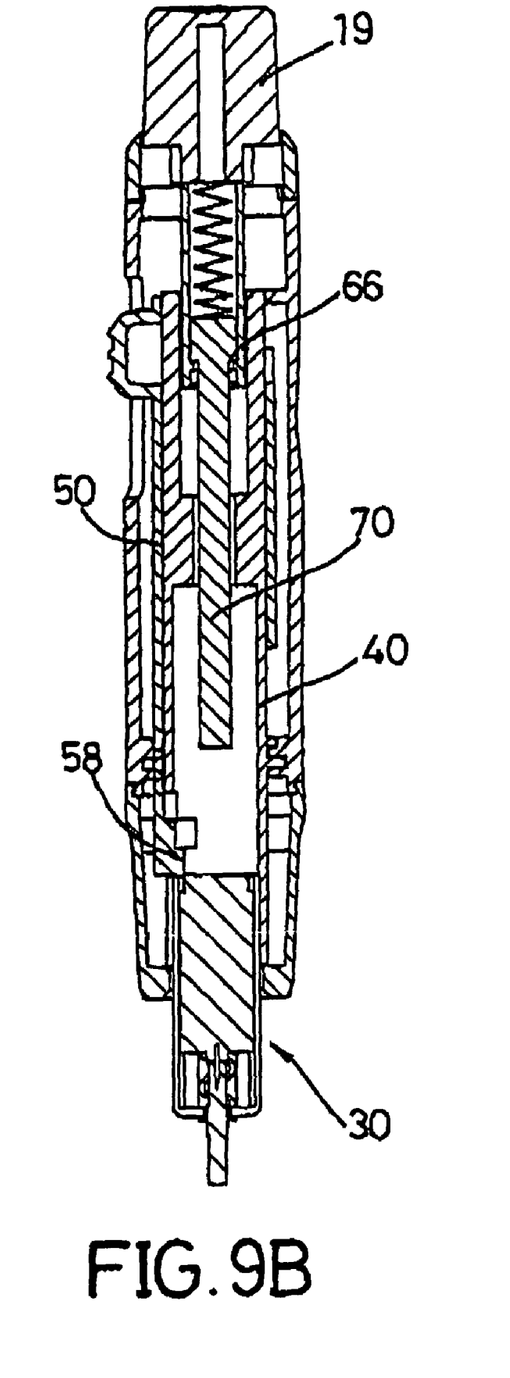
FIG. 9B is an operational cross sectional side view of the safety lancet device in FIG. 9A.

With further reference to FIGS. 9A and 9B, inserting a new needle hub (30) into the proximal open end of the container (40) pushes the rod (56) with the tab (58), the pressing unit (50), the protruding keys (52) of the pressing unit (50), the arc controller tabs (64), the controller (60), the inner annular ring (66) of the controller (60) and the head (71) of the pushing unit (70) until the arced controller tabs (64) stop in the top of the side slot (49) and the arced tabs (72) of the pushing unit (70) are released from the inner surface of the annular protrusion (48) and abut the top of the annular protrusion (48) in the container (40). Continuing to push, the protruding keys (52) of the pressing unit (50) release from the arced controller tabs (64) and return to the original location before use. The safety lancet device is ready for use again.

According to the safety lancet device in accordance with the present invention, the used needle hub must be changed before the safety lancet device can be used again.

Although the invention has been explained in relation to its preferred embodiment, many other possible modifications and variations can be made without departing from the spirit and scope of the invention as hereinafter claimed.

What is claimed is:

1. A safety lancet device comprising:
   a casing;
   a driver assembly mounted in the casing and comprising
      a cylindrical container mounted securely with the casing and comprising
         a cylindrical container proximal open end;
         a distal open end;
         a cylindrical container inner surface;
         a cylindrical container outer surface;
         an outer diameter;
         an inner diameter;
         a cylindrical container middle;
         an annular protrusion formed integrally with and extending inward from the cylindrical container inner surface in the cylindrical container middle and having an annular protrusion inner surface, an inner diameter and a top; and
         multiple side slots formed through the cylindrical container outer surface, between the annular protrusion and the distal open end and each comprising a top and a bottom;
      a cylindrical pressing unit slidably mounted around the distal open end of the container and comprising
         a cylindrical pressing unit proximal end;
         a cylindrical pressing unit distal end;
         an inner diameter corresponding to the outer diameter of the container;
         multiple protruding keys formed integrally with and extending outward from the cylindrical pressing unit distal end and having respectively bottoms; and
         a rod formed on and extending downward from the cylindrical pressing unit proximal end and having a rod free end;
      a cylindrical controller slidably mounted in the distal open end of the container and comprising
         a cylindrical controller proximal end;
         a cylindrical controller distal end;
         an outer diameter corresponding to the inner diameter of the container;
         a cylindrical controller outer surface;
         a cylindrical controller inner surface;
         multiple arced controller tabs corresponding respectively to the protruding keys of the pressing unit and the side slots of the container and having respectively an attached end and an arced tab controller free end, wherein the attached end is formed on and extends from the cylindrical controller outer surface; and
         an inner annular ring formed on and extending radially inward from the cylindrical controller inner surface and near the cylindrical controller distal end and having an inner diameter smaller than the inner diameter of the annular protrusion of the container;
      a pushing unit slidably mounted in the controller and comprising
         a proximal closed end;
         a pushing unit distal closed end;
         an outer diameter smaller than the inner diameter of the inner annular ring in the controller;
         a head formed on and extending upward from the pushing unit distal closed end and having an outer diameter larger than the inner diameter of the inner annular ring in the controller; and
         multiple arced tabs formed on and extending downward from the head and respectively having
            an attached end;
            an arced tab free end; and
            an outer diameter smaller than the inner diameter of the annular protrusion in the container when the arced tab free end abutting the pushing unit; and
      a resilient element mounted between the pushing unit and the casing; and
   a needle hub with a needle slidably mounted in the cylindrical container proximal open end of the container.

2. The safety lancet device as claimed in claim 1, wherein the needle hub comprises
   a needle sleeve comprising
      a needle sleeve proximal open end;
      a needle sleeve distal closed end;
      a needle sleeve inner surface;
      a needle sleeve outer surface;
      a hole formed in the needle sleeve distal closed end; and
      multiple positive limits formed near the needle sleeve proximal open end; and
   a needle core with a needle slidably mounted in the needle sleeve and protruding from the hole.

3. The safety lancet device as claimed in claim 2, wherein the needle sleeve of the needle hub has
   multiple longitudinal grooves formed in the needle sleeve inner surface and the multiple positive limits are formed respectively in the longitudinal grooves near the needle sleeve proximal open end; and
   the needle core has
      a needle core proximal end;
      a needle core distal end;
      a needle core middle;
      a top plate formed on the needle core proximal end and having a top plate outer surface; and multiple protrusions formed on the top plate outer surface of the top plate and corresponding to the longitudinal grooves to limit the needle core in the needle sleeve.

4. The safety lancet device as claimed in claim 3, wherein the needle core has multiple resilient core members attached to the top plate and the needle sleeve distal closed end of the needle sleeve and mounted between the needle core and the needle sleeve.

5. The safety lancet device as claimed in claim 3, wherein
the needle sleeve has multiple flat tapers formed in the needle sleeve inner surface of the needle sleeve distal closed end; and
the needle core has
multiple longitudinal keys formed on and extending outward from the needle core middle of the needle core, and corresponding respectively to the longitudinal grooves to guide the movement of the needle core; and
multiple middle arced tabs formed on the needle core middle and between the longitudinal keys of the needle core and having an attached end and a middle arced tab free end, wherein the middle arced tab free end of the middle arced tabs abuts the taper of the needle sleeve.

6. The safety lancet device as claimed in claim 5, wherein the multiple protrusions respectively have at least one nub formed on and extending outward from the protrusion, and the multiple longitudinal keys respectively have multiple nubs formed on and extending outward from the longitudinal key.

7. The safety lancet device as claimed in claim 6, wherein the needle sleeve has multiple longitudinal flanges formed on the needle sleeve outer surface, and the container has longitudinal recesses formed in the cylindrical container inner surface of the cylindrical container proximal open end and corresponding to the longitudinal flanges of the needle sleeve.

8. The safety lancet device as claimed in claim 7, wherein the needle core further has a detachment joint formed in the needle core middle of the needle core and separates to form a needle point sheath, and the needle is attached in the needle core middle of the needle core and located at the detachment joint.

9. The safety lancet device as claimed in claim 8, wherein the container further has
a slot formed through the cylindrical container proximal open end;
multiple annular flanges formed radially and extending outward from the cylindrical container outer surface near the cylindrical container middle and mounted with the casing;
multiple gaps formed respectively in the corresponding annular flange for mounting the rod of the pressing unit.

10. The safety lancet device as claimed in claim 9, wherein the slot of the container is a cross shape.

11. The safety lancet device as claimed in claim 10, wherein the container further has multiple grooves formed longitudinally in the cylindrical container inner surface of the distal open end for mounting the arced controller tabs of the controller.

12. The safety lancet device as claimed in claim 11, wherein the pressing unit further has a thumb tab formed on and extends outward from the cylindrical pressing unit distal end.

13. The safety lancet device as claimed in claim 12, wherein the rod further has a tab formed on and extending inward from the free end of the rod.

14. The safety lancet device as claimed in claim 13, wherein the controller further has
an annular ring formed radially and extending outward from the cylindrical controller outer surface of the cylindrical controller proximal end of the controller; and
multiple longitudinal ribs formed longitudinally on the cylindrical controller outer surface and connected with the annular ring and the arc controller tabs extending respectively from the longitudinal rib.

15. The safety lancet device as claimed in claim 14, wherein the pushing unit further has a neck formed near the pushing unit distal closed end and the arc tabs are located corresponding to the neck.

16. The safety lancet device as claimed in claim 15, wherein the casing comprises
a front casing comprising
a front casing proximal end;
a front casing distal end;
a front casing inner surface;
a front casing outer surface; and
a guide slot formed longitudinally through the front casing and near the distal end;
a rear casing engaged with the front casing to form a circular casing and comprising a rear casing proximal end, a rear casing distal end, a rear casing inner surface and a rear casing outer surface;
a bottom ring engaged with the proximal ends of the front casing and the rear casing and comprising a bottom ring proximal end and a bottom ring distal end;
a top ring engaged with the distal ends of the front casing and the rear casing; and
a top cap comprising a top cap proximal end and a top cap distal end, wherein the top cap proximal end passes through the top ring and mounted with the pushing unit.

17. The safety lancet device as claimed in claim 16, wherein the front casing further has multiple annular ribs formed radially around and extending inward from the inner surface near the proximal end, and the rear casing further has multiple annular ribs formed radially around and extending inward from the rear casing inner surface near the rear casing proximal end and corresponding to the annular ribs of the front casing.

18. The safety lancet device as claimed in claim 17, wherein
the front casing further has multiple recesses formed around and radially inward from the outer surface respectively of the distal end and the proximal end;
the rear casing further has multiple recesses formed around and radially inward from the rear casing outer surface respectively of the rear casing distal end and the rear casing proximal end and corresponding to the recess of the front casing; and
the bottom ring further has an annular ring formed radially and extending inward from the bottom ring proximal end of the bottom ring and engaged with the recesses of the front casing and the rear casing.

19. The safety lancet device as claimed in claim 18, wherein the controller further has an inner thread formed on the cylindrical controller inner surface of the cylindrical controller proximal end, and the top cap proximal end of the top cap further has a top cap outer surface and a top cap outer thread formed on the outer surface.

* * * * *